US009220743B2

(12) United States Patent
Miller et al.

(10) Patent No.: US 9,220,743 B2
(45) Date of Patent: *Dec. 29, 2015

(54) PAN-ANTIVIRAL PEPTIDES FOR PROTEIN KINASE INHIBITION

(75) Inventors: Kent D. Miller, Ormond Beach, FL (US); Billy S. Austin, Lake Mary, FL (US); Jay E. Yourist, Miami, FL (US)

(73) Assignee: Nuovo Biologics, LLC, Miami, FL (US)

( * ) Notice: Subject to any disclaimer, the term of this patent is extended or adjusted under 35 U.S.C. 154(b) by 1266 days.

This patent is subject to a terminal disclaimer.

(21) Appl. No.: 12/897,087

(22) Filed: Oct. 4, 2010

(65) Prior Publication Data

US 2011/0183884 A1 Jul. 28, 2011

Related U.S. Application Data

(62) Division of application No. 12/691,902, filed on Jan. 22, 2010, now Pat. No. 7,807,635.

(51) Int. Cl.

| A61K 35/583 | (2015.01) |
|---|---|
| C07K 14/435 | (2006.01) |
| A61K 38/16 | (2006.01) |
| C07K 14/00 | (2006.01) |
| A61K 38/00 | (2006.01) |
| A61K 38/17 | (2006.01) |

(52) U.S. Cl.
CPC ............ *A61K 38/005* (2013.01); *A61K 38/1703* (2013.01)

(58) Field of Classification Search
None
See application file for complete search history.

(56) References Cited

U.S. PATENT DOCUMENTS

| 3,888,877 A | 6/1975 | Lehn |
|---|---|---|
| 3,888,977 A | 6/1975 | Sanders |
| 4,126,676 A | 11/1978 | Sanders |
| 4,162,303 A | 7/1979 | Sanders |
| 4,341,762 A | 7/1982 | Haast |
| 4,741,902 A | 5/1988 | Haast |
| 5,182,260 A | 1/1993 | Maraganore et al. |
| 5,565,431 A | 10/1996 | Lipps et al. |
| 5,676,974 A | 10/1997 | Valdes et al. |
| 5,723,477 A | 3/1998 | McDonald et al. |
| 5,859,187 A | 1/1999 | Matthews et al. |
| 5,955,303 A | 9/1999 | Au-Young et al. |
| 5,989,857 A | 11/1999 | Mundschenk |
| 5,994,515 A | 11/1999 | Hoxie |
| 6,613,745 B1 | 9/2003 | Gopalakrishnakone et al. |
| 6,670,148 B2 | 12/2003 | Mundschenk et al. |
| 7,259,237 B1 | 8/2007 | Miller et al. |
| 7,348,400 B2 | 3/2008 | Livett et al. |
| 7,807,635 B1 * | 10/2010 | Miller et al. ................ 514/1.1 |
| 7,902,152 B2 | 3/2011 | Reid et al. |
| 8,034,777 B2 | 10/2011 | Reid et al. |
| 8,940,867 B2 * | 1/2015 | Miller et al. ................ 530/345 |
| 2002/0150975 A1 | 10/2002 | Methfessel et al. |
| 2003/0211465 A1 | 11/2003 | Mundschenk et al. |
| 2004/0077545 A1 | 4/2004 | Lipps et al. |
| 2004/0192594 A1 | 9/2004 | Reid et al. |
| 2005/0031608 A1 | 2/2005 | Reid et al. |
| 2005/0255097 A1 | 11/2005 | Reid et al. |
| 2006/0088843 A1 | 4/2006 | Reid et al. |
| 2006/0088858 A1 | 4/2006 | Reid et al. |
| 2006/0229588 A1 | 10/2006 | Demopulos et al. |
| 2008/0081048 A1 | 4/2008 | Raymond et al. |
| 2008/0107752 A1 | 5/2008 | Reid et al. |
| 2008/0161538 A1 | 7/2008 | Miller et al. |
| 2008/0248992 A1 | 10/2008 | Mundschenk et al. |
| 2008/0254137 A1 | 10/2008 | Raymond et al. |
| 2009/0118503 A1 | 5/2009 | Sprott et al. |
| 2009/0209468 A1 | 8/2009 | Reid et al. |
| 2009/0304710 A1 | 12/2009 | Park et al. |
| 2011/0311642 A1 | 12/2011 | Reid |

FOREIGN PATENT DOCUMENTS

| CN | 1337404 | 2/2002 |
|---|---|---|
| WO | WO 99/24055 | 5/1999 |
| WO | WO 01/70173 | 9/2001 |
| WO | WO 2009/105585 | 8/2009 |

OTHER PUBLICATIONS

Austin, "FELV and FIV Cats Sera-Convert to Negative with PANAVIRA," Journal of the American Holistic Veterinary Medical Association, 2009, vol. 28(1), pp. 28-29.*
Yourist, "Inhibition of Protein Kinases by Antiviral Cobra alpha-Neurotoxoid," Federation Proceedings, 1981, vol. 40, p. 300, Abstract 376.*
Miller, 1979, Workshop on Modified Neurotoxin Treatment of ALS, 62-79.*
Website: http://hhv-6foundation.org/news/cfs-a-herpesvirus-infection-of-the-vagus-nerve, 2 pages, Mar. 30, 2015.*
Website: http://familydoctor.org/familydoctor/en/diseases-conditions/herpes/symptoms.html, 2 pages, Mar. 26, 2015.*
Website: http://www.nhs.uk/Conditions/Tourette-syndrome/Pages/Introduction.aspx, 3 pages, Mar. 31, 2015.*
International Preliminary Report on Patentability for International (PCT) Patent Application No. PCT/US11/22200, mailed Aug. 2, 2012, 7 pages.
Tu, "Neurotoxins of Animal Venoms: Snakes," Ann. Rev. Biochem, 1973, vol. 42, pp. 235-258.
Database WPI, Thomson Scientific, London, GB; AN 2002-384228, XP007217147, & CN 1337404A, Feb. 27, 2002 *abstract*.
Extended Search Report for European Patent Application No. 11735292.2, dated Dec. 6, 2013 7 pages.
He et al., "Cloning and Purification of α-neurotoxins from king cobra (Ophiophagus Hannah)," Toxicon, 2004, vol. 44, pp. 295-303.
Nicastro et al., "Solution Structure of crotamine, a Na- channel affecting toxin from Crotalus durrisus trafficus venom," Eur. J. Biochem., 2003, vol. 270, pp. 1969-1979.
Shiu et al., "Solution Structure of γ-Bungarotoxin: The Functional Significance of Amino Acid Residues Flanking the RGD Motif in Integrin Binding," Proteins: Structure, Function, and Bioinformatics, 2004, vol. 57, pp. 839-849.

(Continued)

*Primary Examiner* — Satyanarayana R Gudibande
(74) *Attorney, Agent, or Firm* — Sheridan Ross P.C.

(57) ABSTRACT

A method of inhibiting protein kinases by administering polypeptides derived from alpha-neurotoxin, and inhibiting protein kinases. Diseases treated thereby include cancer, influenza, Tourette's syndrome, pain, and neurological deficits.

7 Claims, 5 Drawing Sheets

(56) References Cited

OTHER PUBLICATIONS

Austin et al., "FELV and FIV Cats Sera-Convert to Negative with PANAVIRA," Journal of the American Holistic Veterinary Medical Association, vol. 28(1), pp. 28-29.

Bodian et al., "The rate of progression of poliomyelitis virus in nerves," Bulletin of the Johns Hopkins Hospital, 1941, vol. 69, pp. 79-85.

Bracci et al., "Molecular Mimicry Between the Rabies Virus Glycoprotein and Human Immunodeficiency Virus-1 GP120: Cross-Reacting Antibodies Induced by Rabies Vaccination," Blood, 1997, vol. 90(9), pp. 3623-3628.

Burmeister Getz et al., "A Comparison between the Sulfhydryl Reductants Tris(2-carboxyethyl)phosphine and Dithiothreitol for Use in Protein Biochemistry," Anal. Biochem., 1999, vol. 273, pp. 73-80.

Chang et al., "Disulfide isomerization and thiol-disulfide exchange of long neurotoxins from the venom of Ophiophagus hannah," Arch Biochem Biophys, online publication Aug. 2006, vol. 454(2), pp. 181-188.

Chen et al., "A long-form alpha-neurotoxin from cobra venom produces potent opioid-independent analgesia," Acta Pharm. Sin., 2006, vol. 27(4), pp. 402-408.

Crawford et al., "Transmission of Equine Influenza Virus to Dogs," Science, 2005, vol. 310, pp. 482-485.

Crestfield et al., "The Preparation and Enzymatic Hydrolysis of Reduced and S-Carboxymethylated Proteins," The Journal of Biological Chemistry, 1963, vol. 238(2), pp. 622-627.

Fabricant et al., "Nerve growth factor receptors on human melanoma cells in culture," Acad Sci USA, 1977, vol. 74, pp. 565-569.

Gordon et al., "Phosphorylation of acetylcholine receptor by endogenous membrane protein kinase in receptor-enriched membranes of Torpedo californica," Nature, 1977, vol. 267, pp. 539-540.

Gordon et al., "Phosphorylation of Membrane Proteins at a Cholinergic Synapse," Proc. Natl. Acad. Sci., 1977, vol. 263-267.

Huang et al., "A rapid and sensitive assay method for protein kinase," Anal. Biochem., 1976, vol. 72, pp. 593-599.

Iida et al., "Protein kinase activity is associated with CD63 in melanoma cells," J Transl Med, 2005, vol. 3, pp. 42-50.

Johansson et al., "Variation in the Divalent Cation requirements of Influenza A Virus N2 Neuraminidases," J. Biochem., 2003, vol. 134, pp. 345-352.

Kasheverov et al., "Benzophenone-type photoactivatable derivatives of alpha-neurotoxins and alpha-conotoxins in studies on Torpedo nicotinic acetylcholine receptor," J. Recept. Signal Trans. Res., 1999, vol. 19(1-4), pp. 559-571.

Kuo et al., "Cobra polypeptide cytotoxin I and marine worm polypeptide cytotoxin A-IV are potent and selective inhibitors of phospholipid-sensitive Ca2+-dependent protein kinase," FEBS Letters, Mar. 1983, vol. 153(1), pp. 183-186.

Lamb et al., "On the action of venoms of different species of poisonous snakes on the nervous system," Lancet, 1904, vol. 1, pp. 20-22.

Lentz et al., "Amino acid sequence similarity between rabies virus glycoprotein and snake venom curaremimetic neurotoxins," Science, 1984, vol. 226, pp. 847-848.

Lentz, Thomas L., "Structure-Function Relationships of Curaremimetic Neurotoxin Loop 2 and of a Structurally Similar Segment of Rabies Virus Glycoprotein in Their Interaction with the Nicotinic Acetylcholine Receptor," Biochem., 1991, vol. 30, pp. 10949-10957.

Matsuda et al., "In vitro demonstration of neural transmission of avian influenza A virus," J. of General Vir., 2005, vol. 86, pp. 1131-1139.

Miller et al., "Inhibition of Virus-Induced Plaque Formation by Atoxic Derivatives of Purified Cobra Neurotoxins," Biochimica et Biophysica Acta., 1977, vol. 496, pp. 192-196.

Mori et al., "Selective targeting of habenular, thalamic midline and monoaminergic brainstem neurons by neurotropic influenza A virus in mice," Journal of Neuroverology, 1999, vol. 5, pp. 355-362.

Mundy et al., "A randomized controlled study of modified cobratoxin in adrenomyeloneuropathy," Neurology, 2003, vol. 61, pp. 528-530.

Nambiar et al., "Signaling Networks in Cutaneous Melanoma Metastasis Identified by Complementary DNA Microarrays," Arch Dermatol, 2005, vol. 141, pp. 165-173.

Neri et al., "Sequence homology between HIV gp120, rabies virus glycoprotein, and snake venom neurotoxins is the nicotinic acetylcholine receptor an HIV receptor?" Arch Virol., 1990, vol. 114, pp. 265-269.

Ruegg et al., "Reductive Cleavage of Cystine Disulfides with Tributylphosphine," Methods in Enzymol, 1977, vol. 47, pp. 111-116.

Saitoh et al., "Change in state of phosphorylation of acetylcholine receptor during maturation of the electromotor synase in Torpedo marmorata electric organ," Proc. Natl. Acad. Sci., 1981, vol. 78, pp. 4430-4434.

Sanders et al., "Neurotoxoid Interference with Two Human Strains of Poliomyelitis in Rhesus Monkeys," New York Academy of Sciences, 1953, vol. 58, Art. 1, pp. 1-12.

Sela et al., "Reductive Cleavage of Disulfide Bridges in Ribonuclease," Science, 1957, vol. 125, p. 691-692.

Selzer et al., "Protein kinase C isoforms in normal and transformed cells of the melanocytic lineage. Melanoma Research," 2002, vol. 12, pp. 201-209.

Teichberg et al., In vitro phosphorylation of the acetylcholine receptor, Nature, 1977, vol. 267, pp. 540-542.

The Bureau of Biologics, The National Institute of Neurological and Communicative Disorders and Stroke, and Johns Hopkins University: Workshop on Modified Neurotoxin Treatment of Amyotrophic Lateral Sclerosis, 1979, pp. 63-79.

Utkin et al., "[alpha-Neurotoxins and alpha-conotoxins—nicotinic cholinoreceptor blockers]," Bioorg. Khim., 1999, vol. 25(11), pp. 805-810 (article in Russian).

van Heyningen et al., "The fixation of tetanus toxin by ganglioside," J. Gen. Microbiol., 1961, vol. 24, pp. 107-119.

Walkinshaw et al., "Three-dimensional structure of the "long" neurotoxin from cobra venom," Proc. Natl. Acad. Sci. USA, 1980, vol. 77(5), pp. 2400-2404.

Wright et al., "The movements of toxin in the nervous system in experimental tetanus in rabbits," Brit. J. Exp. Path., 1951, vol. 32, pp. 169-182.

Yoon et al., "Influenza virus infection in racing greyhounds," Emerg Infect Dis, 2005, vol. 11, pp. 1974-1976.

Yourist et al., "Inhibition of Protein Kinases by Antiviral Cobra alpha-Neurotoxoid," Federation Proceedings, 1981, vol. 40, p. 300, Abstract 376.

Yourist et al., "Inhibition of Herpes Simplex Virus Replication by Cobra .alpha.-Neurotoxoid," J. Gen. Virol., 1983, vol. 64, pp. 1475-1481.

International Search Report and Written Opinion for International (PCT) Patent Application No. PCT/US11/22200, mailed Mar. 30, 2011.

Hudson et al. "Experimental allergic encephalomyelitis: Prevention with a nontoxic derivative of cobra neurotoxin, MOL." Immunology, 1983, vol. 20, No. 2, pp. 229-232.

Yang et al. "Optical Rotary Dispersion of Cobratoxin," The Journal of Biochemistry, 1967, vol. 61, No. 2, p. 272-274.

* cited by examiner

PAN-ANTIVIRAL PEPTIDES FOR PROTEIN KINASE INHIBITION

CROSS-RELATED REFERENCE SECTION

This application is a divisional application of U.S. patent application Ser. No. 12/691,902, filed Jan. 22, 2010, now U.S. Pat. No. 7,807,635 which is incorporated herein by reference.

BACKGROUND OF THE INVENTION

The present invention relates to inhibition of protein kinases. In particular, the present invention relates to therapeutic uses of polypeptides that inhibit protein kinases.

DESCRIPTION OF RELATED ART

The inventions described herein arose from the pioneering work of Sanders, which documented the antipolio action of detoxified venoms from Elapidae. His work was preceded by the original observations of Bodian and Howe (Bull. Johns Hopkins Hospital, 69: 79-85 (1941)) that proved and measured the retrograde axonal transport of polio viruses to the central nervous system. The latter phenomenon was accomplished by severance of the sciatic nerve in rats at different times following viral infection of the footpads distal to the severed nerves. Sanders was also cognizant of the early studies, by Lamb and Hunter (Lancet, 1: 20-22 (1904)), of the pathology of cobra bites in patients in India, and in experimental animals injected with those venoms. Changes in structures within higher centers of the CNS, including central chromatolysis, occurred within 1-4 hours following cobra envenimation. Further, it was long recognized from clinical observations that rabies viruses, and proteins such as tetanus toxin (Wright et al., Brit. J. Expl. Path. 32: 169 (1951)), appeared to travel to the central nervous system via nerve pathways. From those and other observations Sanders initiated his extensive studies into the ability of neurotoxic snake venoms, detoxified by a specific chemical means, to prevent polio infections in mice, rats and monkeys challenged with poliovirus preparations (Sanders, et al., Ann. N.Y. Acad. Sci. 58: 1-12 (1953)). Those studies were based on what was known at the time as the "interference" phenomenon in which infection with one virus conveys resistance to a second virus acquired a short time later.

With the availability of the Salk vaccine in the early 1950's Sanders polio work was discontinued. He then initiated studies into effects of his medicines on the progressive, irreversible neuromuscular dysfunctions in patients with amyotrophic lateral sclerosis (ALS). His clinical studies employed a Time-Series protocol, the statistical means with which to evaluate drug effects in patients such as those with ALS. By that means he circumvented the ethical problem of placebo administration to patients with a progressive, irreversible disease.

The realization that protein toxins bind strongly to specific receptors on target cells surged with the discovery, by van Heyningen and Miller (J. Gen. Microbial., 24: 107 (1961)), that tetanus toxin binds strongly to gangliosides, chemical constituents of nerve cells. That phenomenon initiated wide-ranging investigations by biochemists into the strong affinities many protein toxins exhibit toward their specific receptors on cells. Further, they identified nontoxic fragments from within the respective protein toxins that retained the cell-binding functions. Such nontoxic, cell-binding fragments offer potential therapeutic and diagnostic opportunities, the goals of many subsequent studies. In 1977 Miller et al., employing separations technology, identified the alpha-neurotoxins in the venoms as precursors of the active principals in Sander's medicine (Biochim. Biophys. Acta, 496: 192-196 (1977)). Exploitation of the phenomenon quickly followed. The amelioration of herpes virus infections in tissue culture systems and in experimental animals was defined by Yourist et al. (J. Gen. Virol., 64: 1475-1481(1983)). Lentz et al., (Biochem., 30: 10949-10957 (1991)) identified constituents on rabies viruses that have amino acid sequences homologous with those in the alpha-neurotoxins. Similar structures also occur in the human immunodeficiency viruses (Bracci et al., Arch. Virol., 114: 265-268 (1990)), also a neurotropic virus.

The ability of the nontoxic peptide preparations to inhibit neurotropic viruses supported Sander's original hypothesis that neurotoxic venom constituents retain affinities for receptor sites on cells, providing one mechanism for the cell protection from those viruses. The surprising discovery that the same nontoxic derivatives of the animal neurotoxins also inhibit the neuraminidases of a number of myxoviruses (Miller and Austin, U.S. Pat. No. 7,259,237, herein incorporated by reference) assigns a second antiviral property to the same peptides. Viral neuraminidases are required for the release of newly formed myxovirus varions from their sites of origin.

The present invention now adds a third mechanism by which the same nontoxic toxin-derived peptides modulate biologic phenomena. They inhibit protein kinases such as those in heart muscle and human myelin as described below.

BRIEF SUMMARY OF THE INVENTION

The present invention provides a method of inhibiting protein kinases, including the steps of administering polypeptides derived from alpha-neurotoxin, and inhibiting protein kinases.

The present invention also provides for treatments of cancer, influenza, Tourette's syndrome, pain, and neurological deficits by the above method.

BRIEF DESCRIPTION OF THE SEVERAL VIEWS OF THE DRAWINGS

Other advantages of the present invention will be readily appreciated as the same becomes better understood by reference to the following detailed description when considered in connection with the accompanying drawings wherein:

FIG. 4 is a graph displaying the chromatographic character of a potassium monopersulfate-oxidized antiviral peptide compared to that of the neurotoxin from which it was derived. A TOSOH TSK-GEL G3000PW column is equilibrated with purified water. After injection of each peptide a linear, aqueous gradient of tetrabutylammonium hydrogen sulfate is applied for 30 minutes to a final concentration of 5 mM.

DETAILED DESCRIPTION OF THE INVENTION

Figure 1:
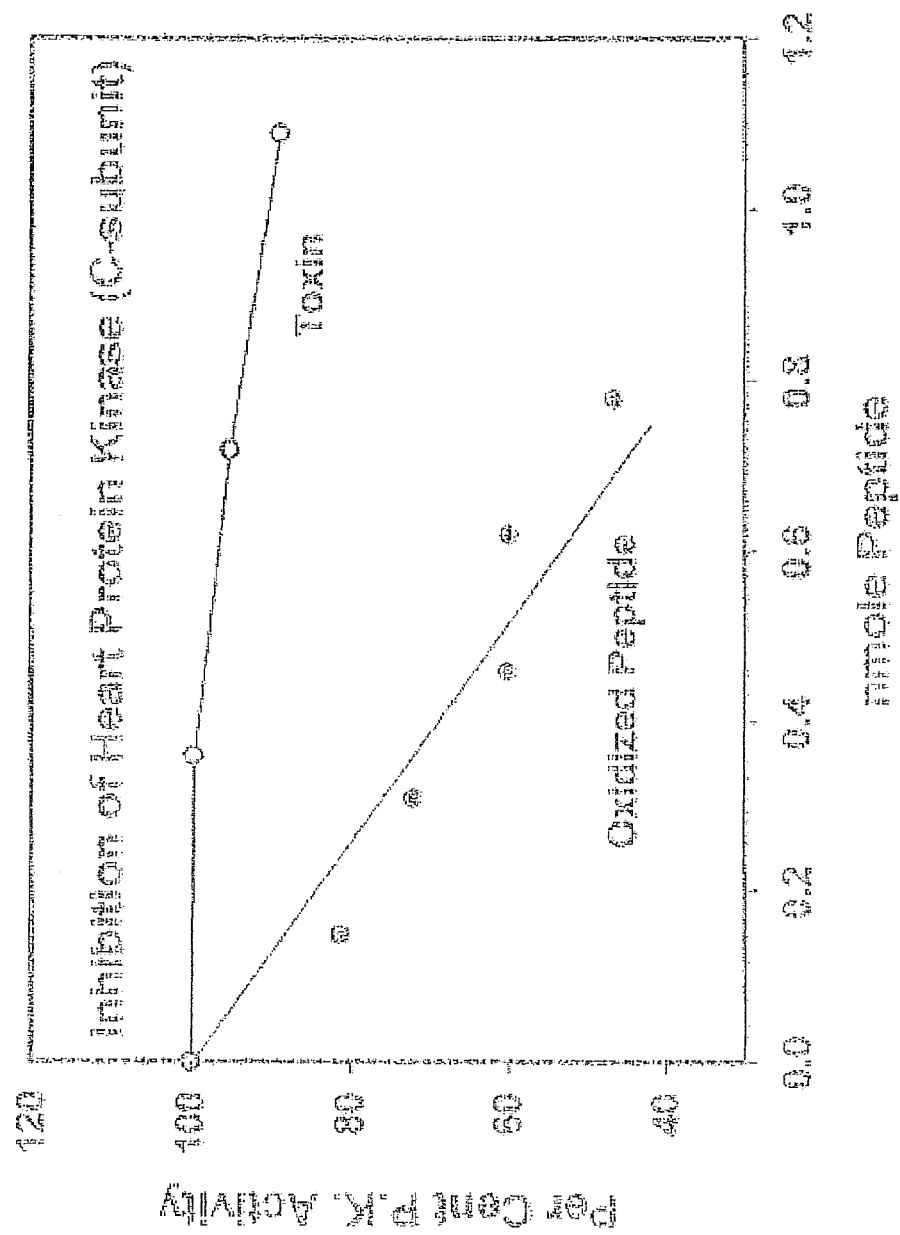
FIG. 1 is a graph displaying the inhibition of the catalytic subunit of purified heart protein kinase A by an oxidized form of the antiviral peptides.
Figure 2:
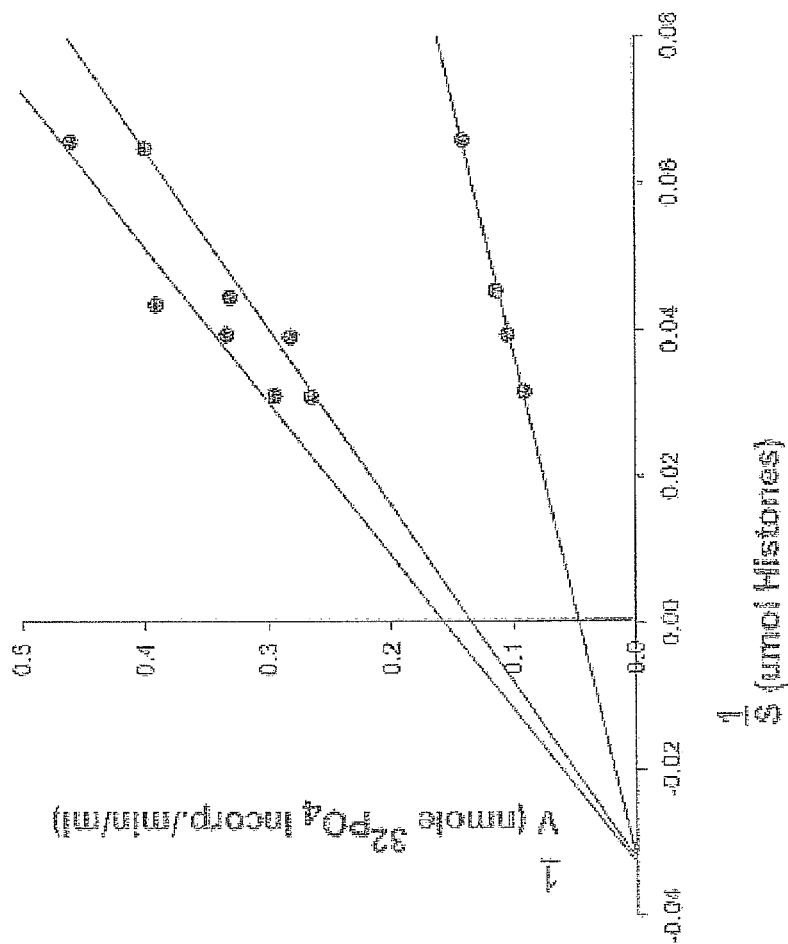
FIG. 2 is a graph that provides a Lineweaver-Burke analysis of effects of varying substrate concentrations on the inhibition of the heart protein kinase A by three concentrations of the oxidized peptide.
Figure 3:
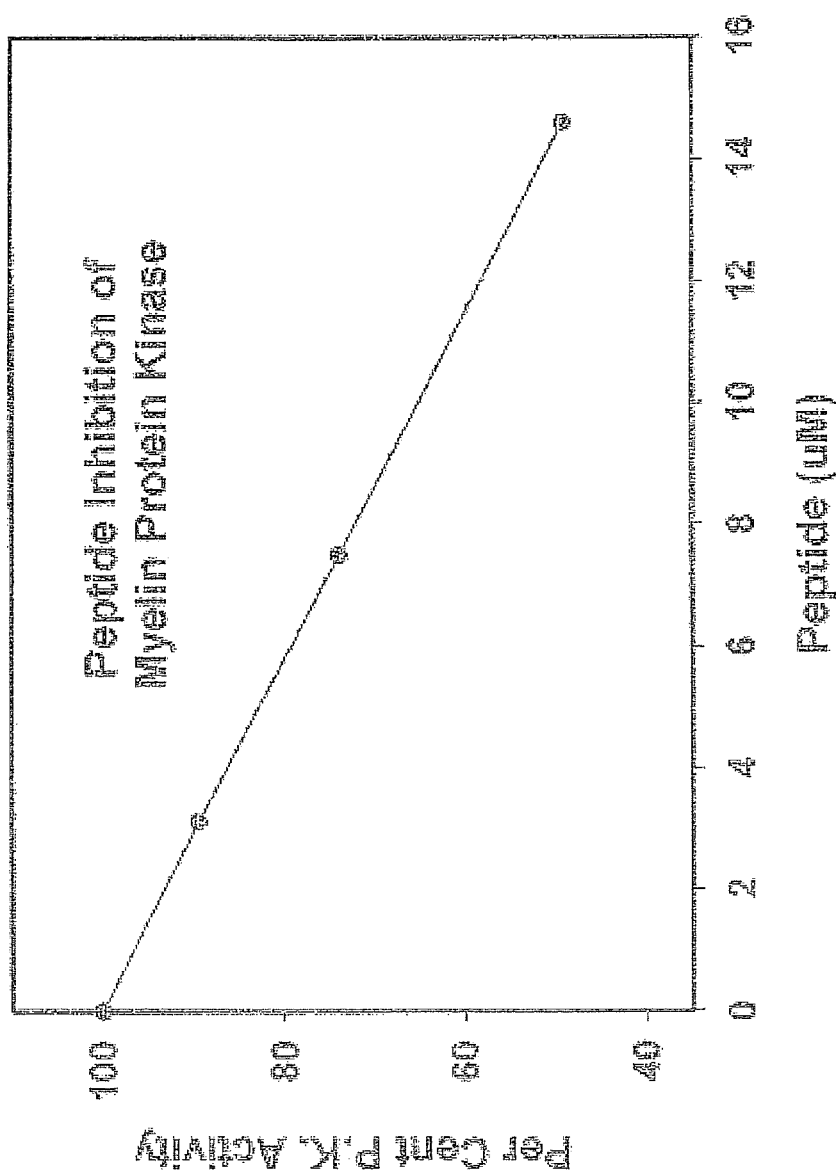
FIG. 3 is a graph that documents inhibition of the cyclic adenosine monophosphate (cAMP) independent protein kinases of purified human myelin, wherein the reaction mixtures are the same as those described for FIG. 1.

The present invention generally provides for a method of inhibiting protein kinases, including the steps of administering polypeptides derived from alpha-neurotoxin, and inhibiting protein kinases.

Important to an understanding of the present invention are the similarities in chemical structures among a wide variety of animal alpha-neurotoxins. Those similarities include closely related amino acid sequences in key parts of the toxin molecules (Yang, C. C., Toxicon, (1974) 12: 1-43). A rigid tertiary conformation of the conserved region after detoxification by disulfide bond scission is suggested by the triple-stranded beta-pleated sheet structure of the native toxin as reported by Walkinshaw (Proc. Nat. Acad. Sci. (1980) 77: 2400-2404).

The polypeptides of the present invention are prepared as described in U.S. Pat. No. 7,259,237 to Applicants. Briefly, alpha-neurotoxin, a precursor molecule, is modified either by specific oxidation of the disulfide bonds, or by specific reduction and subsequent alkylation of the disulfide bonds. Various other modifications can be made to the polypeptides as described in the above referenced patent. The polypeptides are also referred to as PANAVIRA® throughout the application.

Antiviral peptides derived from alpha-neurotoxins are formed by scission of the toxin disulfide bonds with resultant conformational changes and elimination of toxicity. Use of strong oxidants for this purpose is problematic because this may result in modifications of other amino acids in these peptides, especially tyrosine, histidine, tryptophane and lysine, common constituents of the alpha-neurotoxins (Yang, C. C., Toxicon (1974) 12:1-43; Elliott, K. A. C., Ann. Rev. Biochemistry, (1946) 15, 1-34; 15 Thompson, E. O. P. 1 Biochim. Biophys. Acta, (1954) 15, 440; Stahman, M. A. and Spencer, A. K., Biopolymers, (1977) 16, 1299-1306). Such inadvertent reactions induce heterogeneity into the final reaction products.

Therefore, it would be desirable to use selective disulfide bond oxidants to generate antiviral peptides. As detailed below, the oxidant, potassium monopersulfate (E.I. Dupont de Nemours & Co., Wilmington Del.), employed herein, is an alternate reagent that specifically oxidizes the sulfur-containing amino acids, cystine and cysteine, without the undesirable alterations cited above.

Two methods for preparation of these antiviral peptides that inhibit viral neuraminidases involve minimal chemical changes to the parent alpha-neurotoxin molecules, resulting in improved purity. Those methods circumvent problems of prior oxidative procedures; namely, undesirable amino acid modifications and attendant microheterogeneity. Chemical purity of the new antiviral peptides is based on specific scissions of the disulfide bonds within the parent alpha-neurotoxins, with no modifications of other amino acids in those molecules. In other words, the disulfide bonds are selectively chemically modified.

The loss of secondary structure is known to cause alpha-neurotoxins to lose toxicity, as alpha-neurotoxins are dependent on intact disulfide bonds. One of the two forms of the antiviral peptide claimed herein results from specific oxidation of the disulfide bonds employing the oxidizing agent, potassium monopersulfate. Potassium monopersulfate characteristically attacks sulfur atoms such as in disulfide and sulfhydryl groups. It has little effect on other amino acids such as tyrosine, tryptophane, and histidine, the latter group of amino acids also susceptible to modification by less specific oxidizing agents.

An example of preparation of a potassium monopersulfate-oxidized antiviral peptide is as follows. A known weight of the purified alpha-neurotoxin is mixed with 7-16 times its weight of dry potassium monopersulfate powder previously dissolved in purified water to a concentration of 12.8 percent. The mixture is stirred one hour at ambient temperature. Those conditions are adequate for the quantitative detoxification of a toxin molecule containing five disulfide bonds per molecule. The oxidized peptide is then freed of excess potassium monopersulfate by one of several methods. Those methods include the following:

a. Diafiltration employing semi-permeable membranes (i.e., Amicon UM-2 membranes) capable of retaining the peptide with elimination of the filterable low molecular weight products including potassium monopersulfate.

b. Chromatographic procedures on columns containing a gel permeation matrix (i.e., P-4 gel: Calbiochem Corp) capable of exclusion of the peptide and retardation of the low molecular weight residual potassium monopersulfate.

c. A convenient method for separation of the peptide from the potassium monopersulfate involves, first, dilution of the reaction mixture 10-fold with purified water. That dilute solution is applied to a column of octadecyl (C18) silica gel previously equilibrated with purified water. After washing with purified water for removal of the excess potassium monopersulfate, the peptide is eluted from the column with 35 percent reagent grade isopropanol. The eluate is collected in screw-capped glass bottles and extracted four times with n-octanol for removal of the isopropanol. The aqueous phase, which includes the peptide in water, is then extracted four times with pentane for removal of residual octanol. The last two pentane extraction mixtures are placed in the freezer. The pentane is decanted from the frozen, aqueous peptide preparation in each case. Finally, the last traces of pentane are driven off by holding the aqueous peptide solution, uncapped but with porous protection from contamination, at 50 degrees C. Demonstrations of the purity of potassium monopersulfate peptide preparations, and of the alpha-neurotoxin from which they are prepared, are demonstrated by the high performance liquid chromatographic pattern illustrated in FIG. 4.

An alternate means for specific scission of disulfide bonds is through specific reductions, with subsequent alkylations of the resultant sulfhydryl groups with adducts that prevent reoxidation. Such reactions are commonly employed in determination of protein structure (Sela, M., White, F. H., and Anfinsen, C. B., Science, (1957) 691-692; Crestfield, A M., Moore, S., and Stein, W. H., J. Biol. Chem., (1963) 238, 622). While reductions with sulfhydryl compounds such as dithiothreital and beta-mercaptoethanol are commonly employed, the phosphenes used herein represent alternative reductants for the same purpose of reducing the disulfide bonds in proteins (Ruegg, U. T. and Rudinger, J., Methods in Enzymol., (1977) 47, 111-126; Getz, E. B., Xiao, M., Chakrabarty, T., et al, Anal. Biochem. (1999) 273, 73-80).

The present invention also utilizes reduction reactions for generation of antiviral peptides that are viral neuraminidase inhibitors, procedures that likewise avoid inadvertent modifications of chemical groups required for full therapeutic effects. In addition, an important objective of the present invention is to obtain a subset of antiviral peptides utilizing reduction and alkylation based on selection, from a list of alkylating agents, of adducts that block the reoxidation of the disulfide bonds when the excess reductants are removed from the peptides. As detailed below, selections among those adducts can yield compounds that, through introduction of highly sensitive markers, permit (1) detailed studies of the interactions between the respective peptide and the virus preparations, and (2) modulation of interactions with the viral neuraminidases.

Figure 5:
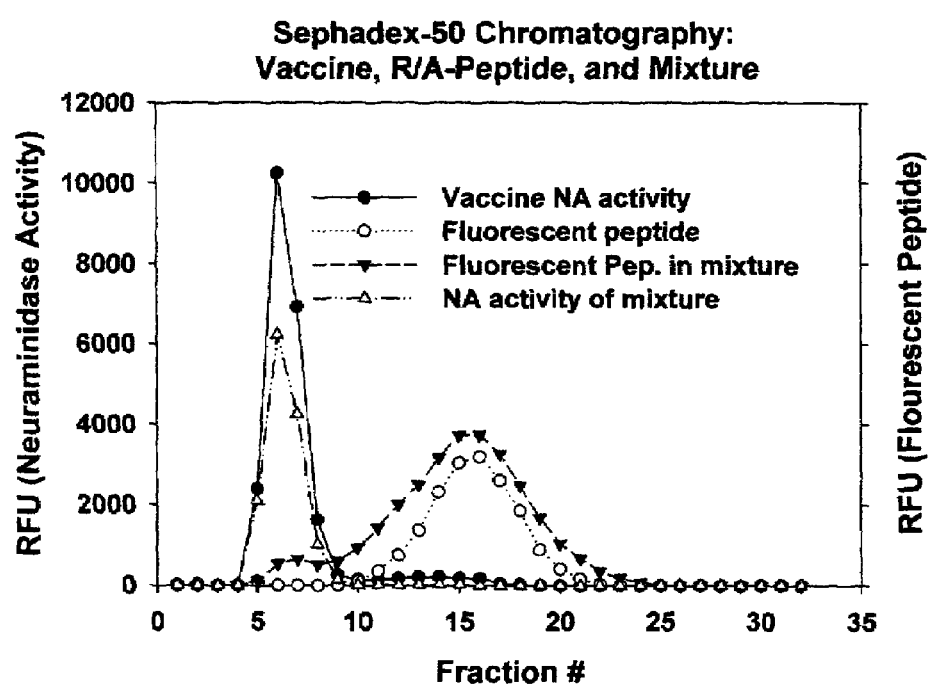
FIG. 5 is a graph displaying the chromatographic characteristics of (1) the neuraminidase activity of the live, canine parainfluenza vaccine, (2) a fluorogenic, reduced, alkylated antiviral peptide (IAEDANS-peptide), and, (3) significantly, the reduction of the neuraminidase activity peak in mixtures of the two reactants at pH 5.5. The chromatographic medium is Sephadex G-50. The solvent is 0.10 M chloride-free acetate buffer, pH 5.5. Fluorescence that reflects the neuraminidase activity of the virus alone and the residual activity in the virus-peptide mixture, are read from the left-hand ordinate. Fluorescence of the IAEDANS-peptide alone, and in the mixture, is read from the right-hand ordinate.

The second new group of viral neuraminidase inhibitors is created by the specific reduction of the disulfide bonds in the precursor neurotoxins. That chemical reaction requires addition of any of a group of blocking reactants that form covalent bonds with the reduced sulfhydryl groups. Such blocking agents (alkylating agents) prevent reoxidation and potential regeneration of toxic activity. Since a number of alkylating agents are available a subset of antiviral peptides are formulated, each a different alkylated derivative of the reduced neurotoxin. Examples of effective alkylating agents are iodoacetamide and iodoacetic acid. Other blocking agents, of major importance to an understanding of the peptide-viral enzyme interactions, insert highly sensitive markers into the basic reduced, alkylated peptide. An example is 5-((((iodoacetyl)amino)ethyl)amino)naphthalene-I-sulfonic acid (IAEDANS). The resultant fluorescent derivative not only retains its ability to inhibit the viral neuraminidases, but also reveals the related formation of complexes between the peptide and a constituent(s) of the respective virus preparation. Evidence further establishes that adducts provided by specific alkylating agents can increase the potency of the antiviral peptides (FIG. 5).

An example of preparation of one of the set of reduced, alkylated antiviral neuraminidase inhibitors is as follows. In this case the purified neurotoxin is dissolved in 6.0 M urea containing 0.01 M ethylenediamine tetraacetic acid buffer, pH 8.0. The solution is degassed with argon, followed by addition of dithiothreital. The mixture is stirred in the dark for 30 minutes for reduction of the disulfide bonds. A blocking compound, one of a variety of choices, is added to alkylate the resultant sulfhydryl groups with the pH maintained at 7.0 with dilute ammonium hydroxide.

An alternate method for preparation of reduced, alkylated antiviral neuraminidase inhibitors involves use of the reducing agent, Tris-(2-carboxyethyl) phosphene. In a dark glass container, a quantity of purified toxin is weighed out and dissolved in 0.1 M HEPES buffer, pH 7.0. The mixture is degassed, purging with nitrogen or argon gas. A weight of Tris-(2 carboxyethyl) phosphene equal to five times the weight of toxin in the solution is added to the mixture. The mixture is stirred in a dark glass vessel for 30 minutes at ambient temperature. The mixture is chilled to 4-6° C., and, with stirring, an amount of dry iodoacetamide, iodoacetic acid, or other alkylation (blocking) agent of choice is added in an amount two to four times the molar quantity of the Tris-(2-carboxyethyl) phosphene in the mixture. After one hour, the mixture is diluted five-fold with purified water. The reduced alkylated mixture is loaded on an octadecyl silica gel column (C18) previously equilibrated with purified water.

After a thorough wash with purified water, the peptide is eluted from the column with 35 percent isopropanol. The aqueous peptide solution is cleared of isopropanol by four extractions with n-octanol followed by four extractions with pentane. The last two pentane extraction mixtures are frozen such that the pentane can be decanted from the frozen, aqueous peptide. The solution is then held at 50 degrees C. to drive off the residual pentane.

Figure 4:
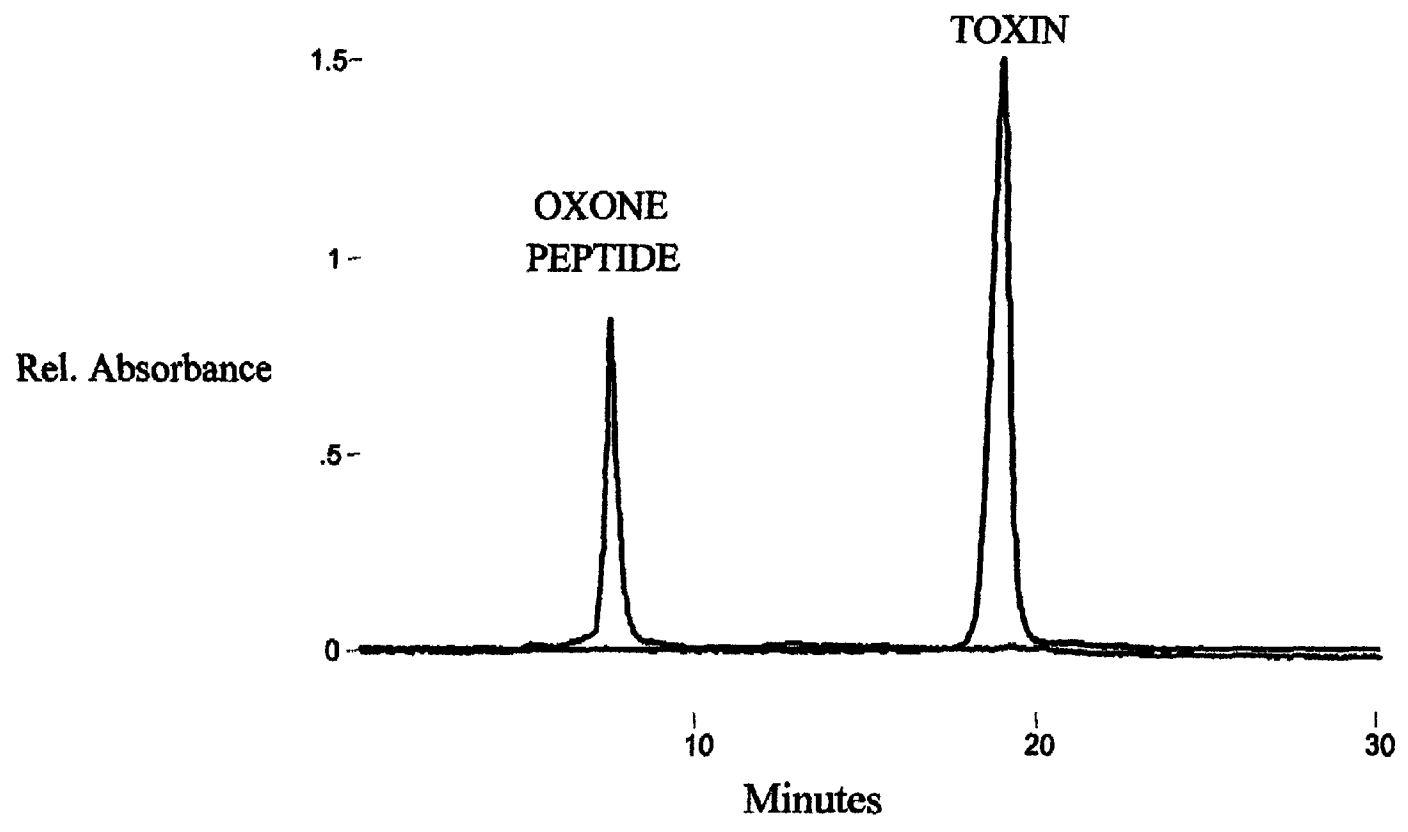

Purity of the nontoxic, antiviral peptide preparations described herein is evaluated by an all-aqueous high performance liquid chromatographic system (HPLC) that clearly distinguishes it from its neurotoxic precursor. An HPLC column, such as a 7.5×300 mm TOSOH TSK-GEL, Type G3000PW, preceded by a 7.5×75 mm guard column of the same material, is thoroughly equilibrated with purified water. After injection of a peptide analyte, a linear gradient to 5 mM tetrabutylammonium hydrogen sulfate is applied over 30 minutes. FIG. 4 exemplifies such separation of a potassium monopersulfate peptide from its neurotoxin precursor.

Protein kinases are enzymes that modify proteins (in general serine, threonine, and/or tyrosine, among other amino acids) by chemically adding phosphate groups to the proteins. Protein kinases regulate the majority of cellular pathways and signal transduction methods. The activity of protein kinases is highly regulated because they have such important effects on cells. Abnormal regulation, i.e. overactivity, of protein kinases often leads to disease. Therefore, it is of interest in the present invention to regulate the function of protein kinases by inhibition.

The ability of the polypeptides to inhibit protein kinases, shown for the first time herein, is one of three mechanisms of action that they possess. Data below shows that protein kinases are inhibited in the heart and myelin. When administered, however, the polypeptides can also function to inhibit viral neuraminidase, cause neurotropism, and combinations thereof. Different mechanisms of action can be required in treating different diseases. These are further detailed below in the examples.

Preferably, the polypeptides are administered by injection once daily to the patient in need thereof. The first dose can be greater (i.e. bolus dose) or less than subsequent doses. In general, 0.2 ml to 0.4 ml of the polypeptides are administered. Further administration methods are described below.

The polypeptides can be used in a method of treating cancer. More specifically, the polypeptides are administered and protein kinases are inhibited. Kinases are commonly activated in cancer cells, such as c-Src, c-Abl, mitogen activated protein (MAP) kinase, phosphotidylinositol-3-kinase (PI3K) AKT, and the epidermal growth factor (EGF) receptor. These kinases are known to contribute to tumorigenesis. Activation of many of the kinases occurs in the same signaling pathway. For example, HER-kinase family members (HER1 [EGFR], HER3, and HER4) transmit signals through MAP kinase and PI3 kinase to promote cell proliferation. The polypeptides are shown to be effective in treating malignant melanoma in the examples below. In malignant melanoma, the polypeptides cause neurotropism as well as inhibition of protein kinases. MAP kinase is down-regulated and serine kinase is inhibited, causing the down-regulation of production of vascular endothelial growth factor (VEGF) and tissue factor (TF). The polypeptides can be used for treating cancers such as, but not limited to, bladder cancer, breast cancer, colon and rectal cancel, endometrial cancer, kidney cancer, leukemia, lung cancer, melanoma, non-Hodgkin Lymphoma, pancreatic cancer, prostate cancer, skin cancer, and thyroid cancer.

The polypeptides can also be used in a method of treating influenza. Besides inhibiting protein kinases, the polypeptides inhibit neuraminidases when treating influenza. Many different types of influenza can be treated, such as, but not limited to, influenza type A, influenza type B, and influenza type C. The influenza can be canine influenza as described in the examples below, and in this case, the neuraminidases inhibited are constituents of myxoviruses.

The polypeptides can be used in a method of treating Tourette's syndrome. Tourette's syndrome is generally characterized by the presence of multiple physical tics and/or vocal tics and speech impediments. Common tics include eye blinking, coughing, throat clearing, sniffing, and facial movements. By inhibiting protein kinases, and more specifically by modulating protein kinase responses to nerve cell stimuli, the polypeptides treat and remove these symptoms.

The polypeptides are also used in a method of alleviating pain, i.e. as an analgesic. The pain can be caused by many different conditions, such as, but not limited to, cancer, neurologic pain, neurological deficits, stroke, chronic fatigue syndrome, and fibromyalgia. By alleviating pain through neurotropism and protein kinase inhibition, the polypeptides allow individuals with these diseases to function in day to day activities such as walking and various motor movements that they previously were unable to do because of pain.

The polypeptides can also be used in a method of overcoming neurological deficits by inhibiting protein kinases. The neurological deficits that are overcome can be any condition that affects nerve function such as neuron communication. Symptoms of neurological deficits include, but are not limited to, weakness, paralysis, impaired hearing or vision, loss or disturbance of sensation, impairment or loss of speech, fixed Dystonia, tremor, Myoclonus, other movement disorders, and Gait problems. The polypeptides can be used to overcome these symptoms. For example, the polypeptides can be used to overcome paralysis. The inhibition of protein kinases can promote recovery of function after paralysis, as shown in the examples below.

The compounds of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compounds of the present invention can be administered in various ways. It should be noted that they can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compounds of the present invention parenterally, they will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439, 196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

EXAMPLE 1

Protein Kinase Inhibition

Searches continued for additional mechanisms by which to explain the range of antiviral actions and other physiologic and clinical effects described in this document. As described in the introduction above both the whole cobra venom and its purified alpha-neurotoxin, detoxified chemically, blocked infections with a variety of neurotropic viruses. Those viruses included polio viruses (Sanders, et al., Ann. N.Y. Acad. Sci.

58: 1-12 (1953)), Semliki Forest Virus (Miller, et al., Biochim. Biophys. Acta, 496: 192-196 (1975)), and herpes viruses (Yourist, Miller, et al., J. Gen. Virol., 64: 1475-1481 (1983)). Alpha-neurotoxins are well known to bind strongly to acetylcholine receptors at myoneural junctions. Also well known is the presence in acetylcholine receptors of a 65 Kd polypeptide that serves as a phosphorylation substrate for protein kinases, a process that is inhibited by cholinergic ligands (Gordon, et al. Nature (1977) 267: 539-540: Teichberg, et al., Nature (1977) 267: 540-542). Since protein kinases mediate cellular responses to events both at the surface and within cells ("signal reactions") investigations centered on effects the nontoxic neurotoxin derivatives have in modulation of protein kinases.

The following systems demonstrate inhibition of both cyclic AMP (cAMP)-dependent and cAMP-independent protein kinases by the antiviral peptides. Reaction mixtures contained varying concentrations of either the purified cobra alpha-neurotoxin or its oxidized, or reduced, alkylated derivatives prepared as described in U.S. Pat. No. 7,259,237. Protein kinase A sources in these assay mixtures included both the commercial heart holoenzyme and its catalytic subunit. Myelin, the source of the cAMP-independent protein kinase C family, was prepared by the procedures of Wu et al. (Biochem. J., 209: 789-795 (1983)). Reaction mixtures (100 μl) also contained 1.0 μmole $MgCl_2$, 1.0 μmole dithiothreital, 200 μg histones as phosphorylation substrates. In the case of the holoenzyme of heart protein kinase A 1.0 nmole cAMP was also added. Urea (10 μmole) was routinely included following demonstration that low urea concentrations prevent polymerizations of the peptides.

Following peptide-enzyme interactions for varying periods the kinase reactions were initiated by additions of 22.5 nmole gamma-32 P-ATP (30 mCi/mmole). After periodic incubations at 37° C., reactions were stopped by additions of 0.02 ml glacial acetic acid. Aliquots (10 μl) of each assay mixture were spotted on instant thin layer chromatography strips. The phosphorylated substrates were then separated from free ATP and measured for radioactive content by the method of Huang and Robinson (Anal. Biochem. 72: 593-599 (1976)). FIG. 1 demonstrates effects of varying concentrations of both the alpha-neurotoxin and its nontoxic, oxidized derivative on the activity of the catalytic subunit of heart protein kinase. FIG. 2 is a Lineweaver-Burke analysis of the rates of inhibition of the catalytic sub-unit of the heart kinase by the oxidized peptide at varying substrate concentrations. FIG. 3 depicts inhibition of the myelin kinase isoforms by the oxidized peptide. Under those same reaction conditions, but without the presence of histones as substrate, the peptides exhibited no uptake of radioactive phosphate. Thus, kinase inhibition is not due to competition by the peptides for phosphorylation sites on the protein substrate.

Confirmation of peptide inhibition of protein kinase A utilized the electrophoretic PK-A assay method of Lutz (Lutz, et al., Anal. Biochem. 220: 268-274 (1994)). Reaction mixtures in 50 microliters of 50 mM HEPES buffer, pH 7.4, (1 mM with respect to EGTA) contained 2-4 units of the catalytic subunit of heart protein kinase A, 8 nmole of kemptide (the PKA substrate), 500 nmole $MgCl_2$, and varying quantities of the oxidized form of PANAVIRA®. Kinase reactions were initiated on additions of 10 nmole ATP. After varying incubation times at 37 degrees C., the reactions were terminated by heat at 93 degrees C. for 5 minutes. Fifty microliters of 0.4 M borate buffer, pH 9.0 (20% with respect to glycerol), were added to each reaction tube, followed by 50 microliters of acetone containing 20 micrograms fluorescamine. After 20 minutes at room temperature for derivatization of the residual kemptide and newly formed kemptide-phosphate, aliquots of the mixtures (15 microliters) were placed in slots in electrophoretic gel plates composed of 0.8% agarose in 50 mM HEPES buffer at pH 8.0. Electrophoresis at 96 V separates the unlabeled and phosphorylated kemptides as, respectively, cathodal and anodal fluorescent bands. Quantitations were by relative fluorescence of the two bands as fractions of that of the respective combined bands.

EXAMPLE 2

Malignant Melanoma

A 12 year-old cocker spaniel presented with a diagnosis of Phase II malignant melanoma. Multiple lesions, malodorous and resembling bunched grapes, emanated from the medial and lateral aspects of the mucocutaneous junction of the right face. The patient was in obvious pain with face swollen and inflamed. Within 24-48 hours following treatment with PANAVIRA® (i.e. the polypeptides prepared according to the method set forth in U.S. Pat. No. 7,259,237) the dog became animated, with lesions less inflamed. After one month of daily PAMAVIRA® treatment the lesions resembled dried raisins surrounded by healthy tissue. The tumors were easily removed, and peptide therapy was continued for an additional month. During the subsequent four years no lesions recurred. On eventual death of the dog from renal failure no detectable tumors were found on autopsy.

The same protocol as described above was subsequently applied to three other dogs with Phase II-III malignant melanomas. Therapeutic outcomes were identical.

Of the three mechanisms of action enjoyed by PANAVIRA®, the combined neurotropism and ability to inhibit protein kinases are responsible for the cures of these animals. Melanocytes are derived from the embryologic neural crest, showing that the neurotropism is reflected in the clinical responses. Melanoma cells, particularly metastatic melanoma cells, are, like nerve cells, rich in receptors for nerve growth factor (NGF) (Fabricant et al., Proc. Natl. Acad. Sci., 74: 565-569 (1977)). However, disorders in protein kinase functions also occur in melanoma cells. That is indicated by presence of a serine kinase activity associated with CD63, a stage-specific melanoma antigen (Iida, J., et al., J. Transl. Med., 3: 42-(2005)). Also, the mitogen-activated protein kinase (MAP) genes are significantly up-regulated in metastatic melanoma cell lines (Nambiar, S, et al., Arch. Dermatology 141: 163-173 (2005)). Further, the MAP kinase itself can up-regulate genes involved in production of the vascular endothelial growth factor (VEGF) and tissue factor (TF), both substances associated with the angiogenesis that supports tumor proliferation (Arbiser, J. L., et al.). The protein kinase assay system that documents peptide inhibition of the myelin protein kinase C, described above, involves inhibition of all isoforms of that enzyme present in the myelin preparations. Selzer et al., (Melanoma Research, 12: 201-209 (2002)) noted that, among the isoforms of the PKC family, the PKG-iota (PKC-i) isoform, was present in all melanoma tumor lysates, melanoma cell lines, and spontaneously transformed melanoma cells, but absent in normal melanocytes. Since some protein kinases are known expression products of oncogenes, substantial attention falls on inhibitors of the kinases. For example, components of the anthrax toxin inhibit the MAP kinase of melanoma cells. PANAVIRA® and its subset of analogues offer similar, safe responses.

EXAMPLE 3

Canine Influenza

A two year-old racing greyhound, partially recovered from a severe bout of flu-like symptoms, retained loud rales in both lungs and continued in a debilitated condition in spite of continuing antibiotics and supportive treatment of various kinds. Canine influenza was diagnosed via blood tests at the Cornell Veterinary Diagnostic Laboratory. PANAVIRA® treatment was then instituted every twelve hours. Recovery was evident within 3-4 days, and treatment was continued for 3-4 months. That dog then won first place in his class approximately six months later. During the same time period canine influenza was diagnosed in two different litters of greyhound pups at the same farm. Twice daily treatments with PANAVIRA® resulted in complete cessation of symptoms in all animals within 4-6 days, and with no recurrences.

Those results support clinical efficacy of PANAVIRA® in canine influenza. Canine influenza represents a recent expansion of the host range of influenza viruses. Common hosts for that virus include fowl, pigs, horses, and humans. Recently Crawford and associates isolated influenza viruses from an outbreak among racing greyhounds in Florida (Science, 310: 482-485 (2005)). Analyses found the virus structure closely related that of the H3N8 equine influenza virus. Identification of the same virus among greyhounds in another geographic region, and similar findings among the general canine population, suggests efficient transmission among the canine population (Yoon, et al., Emerging Infectious Diseases, 11: (1005)). The ability of PANAVIRA® to inhibit the neuraminidases of myxoviruses (U.S. Pat. No. 7,259,237 B1) best explains the responses seen in influenza cases described above.

EXAMPLE 4

Tourettes' Syndrome

A 33 year old male patient experienced the onset of the Tourette Syndrome during the 7-10 year age range. He was treated with Haldol until age 20 at which time that therapy was discontinued because of drug related limitations in life style and constant lethargy. At age 33 he was treated with 0.2 ml of PANAVIRA® intramuscularly. A transitory muscular tingling was noted approximately 45 minutes post injection. Twenty-four hours later the dose was doubled to 0.4 ml I.M. Forty-five minutes after that injection the patient experienced complete cessation of all evidence of Tourette's Syndrome with normalcy maintained at the same daily dosage levels from that day forward. Normalcy is characterized by freedom from tics and speech impediments, and by uninterrupted ability to formulate sentences without hesitation.

Of the three mechanisms of peptide action described above the neurotropic property of the peptide and its ability to modulate protein kinase responses to nerve cell stimuli provide the clinical response in Tourette's Syndrome.

EXAMPLE 5

Pain Associated Conditions

In the course of treatments of animals with varying clinical conditions, the dramatic analgesic effects of the same subset of peptides that exhibit antiviral effects were immediately identified. Regardless of the direct causes of pain, with few exceptions, rapid, dramatic relief of pain is maintained with daily treatments.

Exemplifying alleviation of cancer pain was an eighteen-month-old German Shepherd presenting with a non-weight-bearing front leg due to osteosarcoma. Thirty to forty minutes after an initial peptide treatment he was observed running on all four legs with normal gait. Daily injections maintained that condition until death six months later.

Neurologic pain and/or neurologic deficits present major uses for the peptides apart from their antiviral properties. Some examples include both animal and human conditions. A six-year-old dachshund presented with complete paralysis from the mid-lumbar area with dragging of both rear legs. A tentative diagnosis of prolapsed disk syndrome was made and an initial treatment with the peptide was administered. At a follow-up visit the next day the patient was able to stand, but could not walk. Follow-up injections were given for three days at which time the animal was able to run and play normally.

Three dogs exemplify peptide treatment of stroke with flaccid paralysis. The first dog presented within hours of the stroke event. He was able to stand with help 24 hours after a first peptide injection, and walked normally following the third treatment. The second dog, presented two days after the stroke event, exhibited both paralysis and a severe head tilt. Four days of daily peptide injections enabled the animal to walk. Continued improvements followed daily injections. After one month of daily therapy the head tilt was resolved, thus completing recovery. The third dog was presented approximately two weeks following onset of stroke symptoms. Peptide effects were not as pronounced as in the prior cases. The animal was able to stand up and walk only with help from the owner. No visible responses were noted during three weeks of daily injections. Suddenly, he then struggled to his feet without help. The response from that point onward was dramatic with normal ambulation after seven more daily injections.

An elderly man was given peptide injections for uncontrolled pain associated with a stroke twenty-seven years previously. Pain relief came within thirty minutes of the first dose, and was maintained by daily doses for six months.

A fifty-two year old female underwent a hysterectomy for removal of a large fibroid. Seven weeks later she developed a bladder fistula, which was corrected surgically. Following those surgeries she slept 13-14 hours per day and was continually weak and tired. Physician consultations followed over a two-year period with the ultimate diagnosis of chronic fatigue syndrome and onset of fibromyalgia. With dietary changes and a limited exercise regimen she gradually improved but continued to need 10 hours of sleep each night with restricted daily activity. After her first day of peptide treatment her leg strength began to return. She continued daily injections for six months at which time she had returned to her normal pain-free life-style.

Of the three mechanisms of peptide action described above the neurotropic property of the peptides and their abilities to modulate protein kinase responses to nerve cell stimuli provide the responses to pain described here.

In summary, one polypeptide (and its subset of chemically modified derivatives described in U.S. Pat. No. 7,259,237) express three distinct mechanisms of action; namely, neurotropism, viral neuraminidase inhibition, and mammalian protein kinase inhibition. Those mechanisms help understand the broad range of therapeutic and prophylactic effects described herein. Positive effects are seen in multiple clinical conditions such as in malignant melanoma, canine influenza A infection, Tourette's Syndrome, and analgesic effects in animals and humans. Those clinical applications are in addition to the effective therapies for feline leukemia and feline immunodeficiency viral infections as documented in U.S. Pat. No. 7,259,237.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of alleviating pain in an individual experiencing pain, the method comprising:

a) identifying an individual experiencing pain; and b) administering to the individual a polypeptide selected from the group consisting of:

i) a polypeptide comprising the amino acid sequence of a native α-neurotoxin, wherein the cysteines involved in forming disulfide bonds are oxidized so that they are unable to form disulfide bonds, and wherein the amino acids of the peptide are unmodified except for lacking disulfide bonds; and ii) a polypeptide derived from an α-neurotoxin by reducing the disulfide bonds of the α-neurotoxin with a reducing agent, and then exposing the reduced disulfide bonds to a blocking group to prevent reoxidation of the reduced disulfide bonds.

2. The method of claim 1, wherein said step of administering comprises injecting the polypeptide into an individual.

3. The method of claim 1, wherein the α-neurotoxin is a Type I α-neurotoxin.

4. The method of claim 1, wherein the α-neurotoxin is a Type II α-neurotoxin.

5. The method of claim 1, wherein the α-neurotoxin is from a snake selected from the group consisting of a cobra, a banded krait and a *Crotalus* duressus terrificus.

6. The method of claim 1, wherein the pain is caused by a condition selected from the group consisting of cancer, stroke, chronic fatigue syndrome and fibromyalgia.

7. The method of claim 1, wherein the pain is caused by cancer.

* * * * *